United States Patent [19]
Davidson

[11] Patent Number: 5,370,694
[45] Date of Patent: * Dec. 6, 1994

[54] ZIRCONIUM OXIDE AND NITRIDE COATED ENDOPROSTHESES FOR TISSUE PROTECTION

[75] Inventor: James A. Davidson, Germantown, Tenn.

[73] Assignee: Smith & Nephew Richards, Inc., Memphis, Tenn.

[*] Notice: The portion of the term of this patent subsequent to Jan. 19, 2010 has been disclaimed.

[21] Appl. No.: 5,621

[22] Filed: Jan. 19, 1993

Related U.S. Application Data

[63] Continuation-in-part of Ser. No. 794,826, Nov. 18, 1991, Pat. No. 5,180,394, which is a continuation of Ser. No. 489,373, Mar. 6, 1990, abandoned, which is a continuation-in-part of Ser. No. 385,285, Jul. 25, 1989, Pat. No. 5,037,438.

[51] Int. Cl.⁵ .......................... A61F 2/28; A61F 2/30; A61F 2/32; A61F 2/36
[52] U.S. Cl. ...................... 623/16; 623/18; 623/20; 623/22; 623/23; 623/11; 623/66
[58] Field of Search ............. 623/16, 18, 20, 22, 623/23, 66, 11

[56] References Cited

U.S. PATENT DOCUMENTS

| | | |
|---|---|---|
| 2,987,352 | 6/1961 | Watson . |
| 3,643,658 | 2/1972 | Steinemenan . |
| 3,677,795 | 7/1972 | Bokros et al. . |
| 3,685,059 | 8/1972 | Bokros et al. . |
| 3,969,130 | 7/1976 | Bokros . |
| 4,040,129 | 8/1977 | Steinemann et al. . |
| 4,145,764 | 3/1979 | Suzuki et al. . |
| 4,159,358 | 6/1979 | Hench et al. . |
| 4,223,412 | 9/1980 | Aoyagi et al. . |
| 4,495,664 | 1/1985 | Blanquaert . |
| 4,608,051 | 8/1986 | Reck et al. . |
| 4,617,024 | 10/1986 | Broemer et al. . |
| 4,652,459 | 3/1987 | Engelhardt . |
| 4,652,534 | 3/1987 | Kasuga . |
| 4,671,824 | 6/1987 | Haygarth . |
| 4,687,487 | 8/1987 | Hintermann . |
| 4,714,474 | 12/1987 | Brooks, Jr. et al. . |
| 4,728,488 | 3/1988 | Gillett et al. . |
| 4,750,903 | 6/1988 | Cheng . |
| 4,769,031 | 9/1988 | McGough et al. . |
| 4,778,461 | 10/1988 | Pietsch et al. . |
| 4,834,756 | 5/1989 | Kenna . |
| 4,888,011 | 12/1989 | Kung et al. . |
| 4,902,291 | 2/1990 | Kolff . |
| 4,955,911 | 9/1990 | Frey et al. . |
| 4,981,484 | 1/1991 | Holfert et al. . |
| 4,994,078 | 2/1991 | Jarvik . |
| 5,037,438 | 8/1991 | Davidson . |
| 5,066,300 | 11/1991 | Isaacson et al. . |
| 5,152,794 | 10/1992 | Davidson . |
| 5,180,394 | 1/1993 | Davidson ........................ 628/16 |

FOREIGN PATENT DOCUMENTS

| | | |
|---|---|---|
| 770080 | 10/1967 | Canada . |
| 1140215 | 1/1983 | Canada . |
| 38902 | 11/1981 | European Pat. Off. . |
| 0159410 | 12/1984 | European Pat. Off. . |
| 1943801 | 4/1970 | Germany . |
| 2811603 | 9/1979 | Germany . |
| 1325269 | 8/1973 | United Kingdom . |

OTHER PUBLICATIONS

Akins, Cary W., "Mechanical Cardiac Valvular Prostheses," Current Review by the Society of Thoracic Surgeons, vol. 52 pp. 161–172 (1991).

(List continued on next page.)

Primary Examiner—Jerome L. Kruter
Assistant Examiner—Dinh X. Nguyen
Attorney, Agent, or Firm—Pravel, Hewitt, Kimball & Krieger

[57] ABSTRACT

Medical implants of zirconium or zirconium-based alloy coated with blue or blue-black zirconium oxide or zirconium nitride to provide low friction, highly wear resistant coatings especially useful in hemiarthroplasty applications such as unipolar artificial joints, including unipolar hip joints or surface replacements, knee joints, shoulder joints, elbows, spinal segments, fingers, etc. The zirconium oxide or nitride coated prostheses also provide a barrier against implant corrosion caused by galvanic coupling with other metal components or in vivo ionization of the metal prosthesis.

17 Claims, 2 Drawing Sheets

OTHER PUBLICATIONS

Baruah Bileaflet Mechanical Cardiac Valve Prosthesis, "Instructions for Use" brochure (date unknown).

G. Bertrans et al "Morphology of Oxyde Scales Formed on Titanium," vol. 21, Oxidation of Metals, Nos. ½ (1983) pp. 1-19.

R. C. Bill, "Selected Fretting-Wear-Resistant Coatings for Ti-6%Al-4% Alloy," Wear 106 pp. 283-301 (1985).

Bradhurst and Heuer, "The Influence of Oxide Stress on the Breakaway Oxidation of Zircaloy-2", J. of Nuclear Materials 37, 35-47 (1970).

Bricoe, et al., "The Friction and Wear of High Density Polyethylene: The Action of Lead Oxide and Copper Oxide Fillers" Wear, 27, 19-34 (1974).

Brown and Merrit, "Evaluation of Corrosion Resistance of Biology," Dept. of Biomedical Engineering, Case Western Reserve University, 13 Feb. 1986 (1:8).

K. G. Budinski, "Tribological Properties of Titanium Alloys," pp. 289-299, vol. 1 *Wear of Materials*, ASME (1991).

Coll and Jacouot, "Surface Modification of Medical Implants and Surgical Devices Using TiN Layers" Surface and Coatings Technology 36, pp. 867-878 (1988).

Conte, Borello and Cabrini, "Anodic Oxidation of Zircaloy-2", Jnl. of Applied Electrochemistry, vol. 6 pp. 293-299 (1976).

Davidson, Schwartz, Lynch, and Gir. "Wear, Creep and Frictional Heating of Femoral Implant Articulating Surfaces and the Effect on Long-Term Performance—Part II, Friction, Heating, and Torque," Jnl. of Biomedical Materials Research: Applied Biomaterials, vol. 22, No. A1, pp. 69-91.

Demizu et al., "Dry Friction of Oxide Ceramics Against Metals: The Effect of Humidity", Tribiology Transactions vol. 33, 4, pp. 505-510 (1990).

Golomb, Gershon, et al "Prevention of Bioprosthetic Heart Valve Tissue Calcification by Charge Modification: Effects of Protamine Binding by Formaldehyde," vol. 25 Jln of Biomedical Materials Research pp. 85-98 (1991).

Haygarth and Fenwick, "Improved Wear Resistance of Zirconium by Enhanced Oxide Films," Thin Solid Films, Metallurgical and Protective Coatings, vol. 118, pp. 351-362 (Apr. 1984).

Khruschov, "Principles of Abrasive Wear," 28, 69-88 (1974).

Kowbel, Witold et al, "Effect of Boron Ion Implantation of Tribological Properties of CVD $Si_3N_4$," vol. 46 Lubrication Engineering, 10 pp. 645-650.

Mäusli et al., "Constitution of Oxides on Titanium Alloys for Surgical Implants" Advances in Biomaterials, vol. 8, pp. 305-310 (1988).

Robert B. More, Malcolm D. Silver; "Pyrolytic Carbon Prosthetic Heart Valve Occluder Wear: In Vivo vs. In Vitro Results for the Bjork-Shiley Prosthesis;" *Journal of Applied Biomaterials, vol. 1, pp. 267-278 (1990)*.

Leo O'Connor, "Novacor's VAD: How to Mend a Broken Heart," Mechanical Engineering pp. 53-55 (Nov. 1991).

Rabinowicz, "Lubrication of Metal Surfaces by Oxide Films" Asle Translations, 10, 400-7 1967.

Rokicki, "The Passive Oxide Film on Electropolished Titanium" pp. 69-70 (Feb. 1990).

Pamphlet, "Zircadyne Corrosion Properties," Teledyne WAH Change Albany (no date) pp. 1-16.

Viegas, et al, "Metals Materials Biodegradation: A Chronoamperometric Study," Jnl. of Materials Science: Materials in Medicine 1, pp. 105-109, (1990).

Weightman and Light, "The Effect of the Surface Finish of Alumina and Stainless Steel on the Wear Rate of UHMW Polyethylene" Biomaterials, 7, 20-24 (Jan. 1986).

"The Cementless Fixation of Hip Endoprostheses," edited by Morscher.

ASTM F86-84, "Standard Practice for Surface Preparation and Marking of Metallic Surfical Implants," pp. 12-14 (1984), corrected editorially in May, 1987.

Author unknown, "Boric Acid: A Self-Replenishing Solid Lubricant," Tech Spotlight, Advanced Materials and Processes pp. 40-42 (Jul. 1991).

Derwent English Translation of Abstract from EP Patent 0,159,410.

Author unknown, "Replacing the Human Heart," Machine Design, pp. 100-107 (Nov. 1991).

"Increase in Biocompatibility of Polymers by Treatment with Phosphatidyl Choline" Study Done by Biocompatibles Ltd. UK and Wolfson Centre for Materials Technology Brunel University 1991.

ZIRCONIUM OXIDE AND NITRIDE COATED ENDOPROSTHESES FOR TISSUE PROTECTION

SPECIFICATION

This application is a continuation-in-part of U.S. Ser. No. 794,826 filed Nov. 18, 1991, U.S. Pat. No. 5,180,394 issued Jan. 19, 1993 which is a continuation of U.S. Ser. No. 489,373 filed Mar. 6, 1990, abandoned which is in turn a continuation in part of U.S. Ser. No. 385,285, filed Jul. 25, 1989, now U.S. Pat. No. 5,037,438.

BACKGROUND OF THE INVENTION

1. Field of Invention

This invention relates to metallic orthopedic implants with load bearing surfaces coated with a thin, dense, low friction, highly wear-resistant coating of blue-black zirconium oxide, black zirconium oxide or zirconium nitride. These coatings are especially useful on the portions of these prostheses which bear against softer surfaces such as body tissue surfaces.

In the preferred oxidation process by which a zirconium oxide coating is produced, the associated increase in surface oxygen content and hardness increases the strength of the metal substrate and improves the fatigue properties of the implant. The oxide or nitride surfaces, being ceramic, do not release potentially harmful metal ions into the body and are not subject to galvanic corrosion in vivo. Further, the ceramic surfaces have enhanced hemocompatibility.

2. Description of the Related Art

Orthopedic implant materials must combine high strength, corrosion resistance, low friction and wear, and tissue compatibility. The longevity of the implant is of prime importance especially if the recipient is relatively young because it is desirable that the implant should function for the complete lifetime of a patient. Because certain metal alloys have the required mechanical strength and biocompatibility, they are ideal candidates for the fabrication of prostheses. 316L stainless steel, chrome-cobalt-molybdenum alloys and more recently titanium alloys have proven to be suitable materials for the fabrication of load-bearing prostheses.

One of the variables affecting the longevity of load-bearing implants such as hip-joint implants is the rate of wear of the articulating surfaces and long-term effects of resultant metal ion release. Such implants may be in the form of a surface replacement which is attached over the neck region of the original femur or a hip-joint prosthesis which has a femoral head attached to a stem portion which is fixed within the proximal shaft of the femur. A typical hip-joint prosthesis for total hip replacements includes a stem, a femoral head, and an acetabular cup against which the femoral head articulates. In the case of hemiarthroplasty, the natural acetabulum is retained so that the prosthetic femoral head articulates against natural body cartilage which is much softer than either metals or ceramics used to fabricate femoral heads. In total hip replacement, wear of either or both of the articulating surfaces results in an increasing level of wear particulates and "play" between the femoral head and the cup against which it articulates. Wear debris can contribute to adverse tissue reaction leading to bone resorption, and ultimately the joint must be replaced.

Generally, in hip hemiarthroplasty the upper (proximal) portion of the natural femur is replaced with a surface replacement or a prosthesis bearing a femoral head for cooperating slidingly with the cartilaginous material in the acetabulum of the natural hip, which is not replaced with the usual prosthetic acetabular cup. This softer cartilage tissue is then subjected to sliding wear induced by the action of a hard unipolar femoral head prosthesis.

The rate of wear of acetabulum cartilage and femoral head surfaces after hemiarthroplasty is dependent upon a number of factors which include the relative hardness and surface finish of the materials which constitute the femoral head, the susceptibility of the head material to ionization and galvanic corrosion, the frictional coefficient between the materials of the head, and cartilage, the load applied and the stresses generated at the articulating surfaces, among other factors. The most common material currently used in the fabrication of hemiarthroplasty hip-joint implants include femoral heads of stainless steel or cobalt or titanium alloys and femoral heads of polished alumina. Of the other factors which influence the rate of wear of hemiarthroplasty hip-joint implants, the most significant are patient weight and activity level.

In the case of a metallic unipolar femoral head, sliding action of femoral head against acetabulum cartilage may gradually erode passive oxide film on its surface and expose body tissue to metal which could lead to release of metal ions and adverse tissue reaction. A ceramic unipolar femoral head, on the other hand, has undesirably a much higher modulus than even metals and is not as impact resistant or shock absorbent as bone or metal. Thus, ceramics while producing lower friction and being usually more biocompatible than metals, suffer significant drawbacks with respect to shock absorbance and impact resistance.

U.S. Pat. No. 4,145,764 to Suzuki et al recognized that while metal prostheses have excellent mechanical strength they tend to corrode in the body by ionization. Suzuki et al also recognized the affinity between ceramics and bone tissue, but noted that ceramic prostheses are weak on impact resistance. Suzuki et al therefore proposed a metal prosthesis plasma sprayed with a bonding agent which is in turn covered with a porous ceramic coating which would allow the ingrowth of bone spicules into the pores. This combination, it was said, would provide both the mechanical strength of metals and the biocompatibility of ceramics. The application of ceramic coatings to metal substrates often results in non-uniform, poorly-bonded coatings which tend to crack due to the differences in thermal expansion and hardness mismatch between the ceramic and the underlying metal substrate. Furthermore, such coatings are relatively thick (50–300 microns) and relatively porous, and since the bond between the metal and the ceramic coating is often weak there is always the risk of galling or separation of the ceramic coating.

U.S. Pat. No. 3,677,795 to Bokros is directed to the application of a carbide coating over a metallic prosthetic device. This method of forming the carbide coating requires that the prosthesis be heated to temperatures of at least about 1350° C. in a reaction chamber through which a hydrocarbon gas such as propane or butane flows. The method is said to produce a prosthetic device which has "excellent compatibility with body tissue and is non-thrombogenic." Bokros does not address the issues of friction, heating, creep and wear of orthopedic implant bearing surfaces, or changes induced in the mechanical properties of the underlying metal due to this high-temperature treatment. Carbonaceous coatings are much less ionic than oxide ceramic coatings (particularly $ZrO_2$ and $Al_2O_3$) and are thus less wettable and produce higher friction.

U.S. Pat. No. 3,643,658 to Steinemann is directed to titanium implants coated with titanium oxide, nitride, carbide or carbonitride to prevent corrosion and abrasion of the implant. These coatings are also said to protect the titanium implant from fretting wear. The coatings vary in thickness from 0.08 microns to about 0.15 microns. Titanium oxide forms naturally on titanium and titanium alloy in ambient conditions. Titanium oxide coatings are not well attached, are not dense and adherent, and are not effective as protective coatings to prevent metal ion release into the body. The oxide film is thin (0.5–7 nm) to a point where it is transparent to the naked eye and is similar to the protective passive oxide layers in cobalt alloys and stainless steels formed primarily from the chromium content. These types of natural passive oxide layers formed under ambient conditions or by nitric acid passivation (usually used for metal orthopaedic implants) can easily abrade off from motion and contact against surrounding material, even soft polymeric materials or body tissue. Under these conditions, metal ions are released into the body environment. For the case of titanium and titanium alloys, amorphous titanium monoxide (TiO) forms at room temperature with small quantities of $Ti_3O_5$. The oxide is easily disturbed in a saline environment resulting in repassivation of an intermediate oxide $3Ti_2O_3.4TiO_2$. Formation of the higher oxide, $TiO_2$ (anatase) and $Ti_2O$ occur at higher oxidation temperatures. However, under fretting conditions (with adjacent bone, bearing against polyethylene, and particularly against metal as in the case for bone screws in bone plates, etc.) all forms of normal passivated, and even high-temperature (350° C.) surface anodized titanium oxide films provide little, if any, protection from spalling of the oxide and subsequent fretting of the metal substrate. Relatively thicker coatings using high current-density anodizing also provide little anti-fretting protection due to the poor adherence of the loose powdery films. In general, titanium oxide films are ineffective against fretting conditions because of their poor strength and attachment.

A totally inert, abrasion resistant monolithic ceramic may be ideal for eliminating fretting and metal ion release. For example, zirconium dioxide ($ZrO_2$) and alumina ($Al_2O_3$) have been shown to be highly inert, low friction, biocompatible implant materials. These ceramics have been in use recently as monolithic alumina or zirconium dioxide femoral heads in total hip replacements. Both materials are hard, dense, biocompatible, lubricous, and sufficiently strong. Importantly, when polished, the highly ionic, wettable ceramic bearing surface, articulating against ultra high molecular weight polyethylene (UHMWPE), not only significantly reduces the frictional moment against the UHMWPE cup but also greatly reduces the rate of wear of the UHMWPE. Similarly, monolithic ceramic femoral heads have been implanted after hemiarthroplasty so that ceramic surfaces cooperate slidingly against natural cartilage of the acetabulum. However, solid ceramics have high modulus and low shock absorbance so that ceramic implants stress shield surrounding bones leading to bone decalcification and resorption while at the same time transmitting relatively higher shock forces to these bones. Beneficially, during articulation, no metal ions or micron-size fretted particulates from the ceramic are produced. Thus, these ceramics have certain advantages over cobalt, stainless steel, and titanium alloy bearing surfaces but also have significant disadvantages.

There exists a need for a hemiarthroplasty orthopedic implant having low friction, highly wear and corrosion resistant load bearing surfaces which may be implanted for the lifetime of the recipient. Further, the bearing surfaces should not cause wear and damage to the natural cartilage of the acetabulum or excessive stress shielding of bone that results in bone resorption and decalcification. Thus, the hemiarthroplasty implant should desirably have a modulus of elasticity closer to that of bone than monolithic ceramics while at the same time possessing low friction and not being susceptible to metal ion release, found in the case of metal implants.

SUMMARY OF THE INVENTION

The invention provides zirconium or zirconium-containing metal alloy hemiarthroplasty implants (endoprostheses) coated with zirconium nitride or blue-black or black zirconium oxide. The zirconium oxide or nitride coating provides the invention prosthesis with a thin, dense, low friction, wear resistant, biocompatible surface ideally suited for use on articulating surfaces of joint prostheses wherein a surface or surfaces of the joint articulates, slides, translates or rotates against a mating joint surfaces, of natural body tissue, such as cartilage. The zirconium oxide or nitride coating may therefore be usefully employed on femoral surface replacements or the femoral heads of hemiarthroplasty ("unipolar") hip implants, femoral or tibial components of knee implants, shoulder (humeral or glenoid) implants, finger implants, etc. In the case of femoral heads designed to cooperate against living cartilage, zirconium or zirconium alloy heads may be coated with zirconium nitride or blue-black or black zirconium oxide to provide a low friction surface for cooperating with the cartilage while at the same time providing better shock absorbance than a solid ceramic head or currently used steel, cobalt alloy, or titanium alloy heads, and eliminating the release of metal ions, as may occur when metal heads are used. Since the underlying material of the femoral head is metal (zirconium and its alloys), the head has a lower modulus than ceramics and thus less tendency to stress shield surrounding bones. Further, zirconium and zirconium alloys have elastic moduli less than stainless steel, cobalt alloy, or titanium alloys currently utilized in joint replacements.

When a zirconium nitride or oxide-coated joint surface is employed to articulate or rotate against cartilage, the low friction characteristic of the coating causes reduced friction, metal ion release, wear, and shock loading relative to prior art prostheses.

The zirconium oxide or nitride coatings of the subject invention are also useful in providing a biocompatible, inert ceramic barrier between the zirconium-containing metal alloy-based prosthesis and body fluids. Thus, since the zirconium oxide or nitride surface is not prone to ionization and galvanic or wear-induced corrosion, both the life span and the biocompatibility of the prosthesis are enhanced.

Additionally, the preferred natural in situ formation of a hard, dense zirconium oxide coating from the metal zirconium (in the substrate) involves oxygen diffusion into the metal substrate below the oxide coating. Oxygen, an alloying constituent in zirconium and zirconium alloys increases the strength and hardness of the metal substrate immediately beneath the hard $ZrO_2$ ceramic surface layer and subsequently increases the fatigue strength. Resistance to fatigue loading is paramount in many orthopedic implant applications such as the hip stem, and femoral and tibial knee components. This hard, strong oxygen-rich metal beneath the surface oxide also provides an interlayer which optimizes the attachment of the $ZrO_2$ surface layer, unlike overlay coating methods, such as plasma spraying or chemical or physical vapor deposition methods. Thus, not only does the formation of the zirconium oxide coating improve wear, friction, and corrosion resistance, it also improves the ceramic coating attachment strength and mechanical integrity of the implant device from a strength standpoint.

DETAILED DESCRIPTION OF THE PREFERRED EMBODIMENTS

The present invention provides low friction, wear resistant coatings on the articulating surfaces of hemiarthroplasty prosthetic devices. An illustrative example of such articulating surfaces is shown in the schematic diagram, FIG. 1A.

In general, the invention provides blue-black or black zirconium oxide and zirconium nitride coated prostheses of zirconium or its alloys, said prostheses being adapted for insertion into two-component joints to replace one component and cooperate with the other natural body tissue component. The two-component joints include hip joints, knee joints, fingers, elbows, shoulders, spinal, and the like. The surgical removal of one component of the joint is termed "hemiarthroplasty" and because the repaired joint has only one artificial (prosthesis) component, the artificial component is often termed a "unipolar" prosthesis, or "endoprosthesis."

Figure 1A:
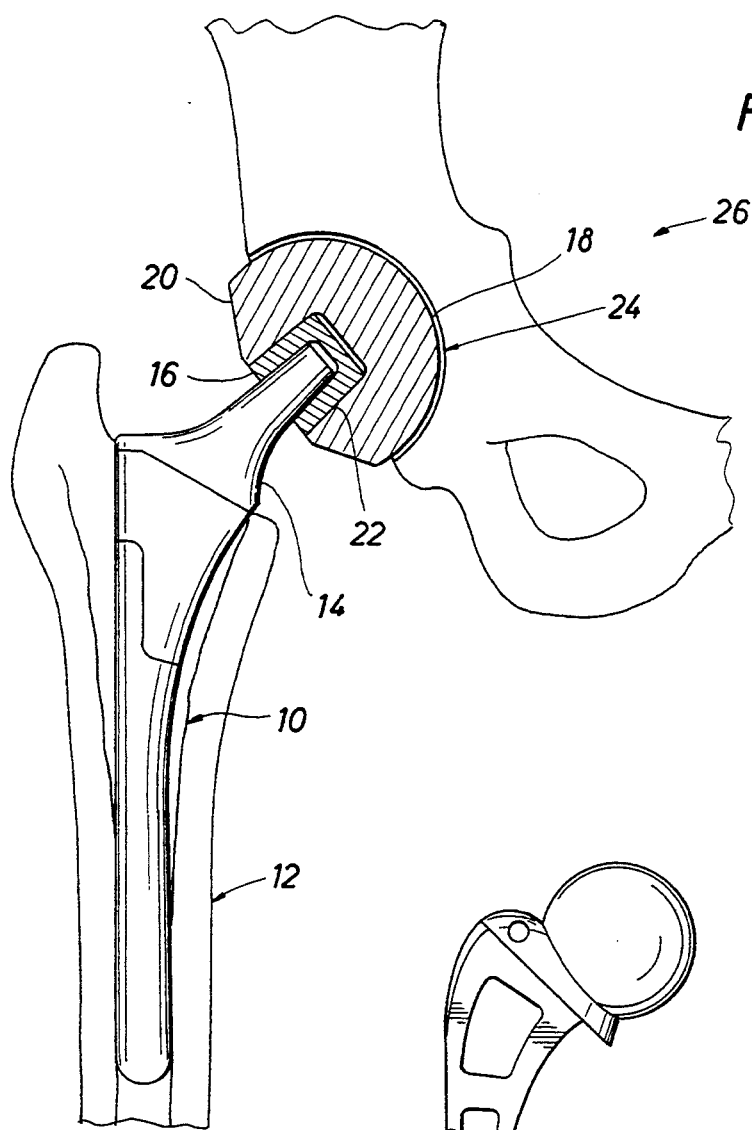
FIG. 1A is a schematic diagram of a hip joint endoprosthesis showing the femoral head (with hip stem and sleeve) cooperating with cartilage of a hip structure.
Figure 1B:
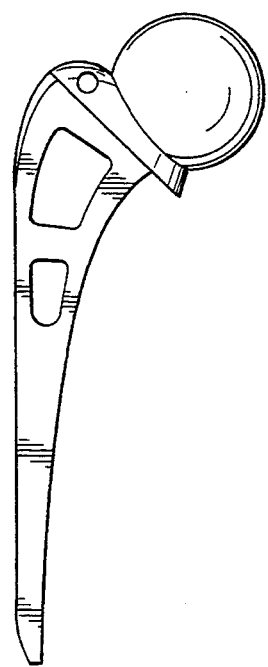
FIG. 1B is another example of a typical hip joint endoprosthesis.
Figure 1C:
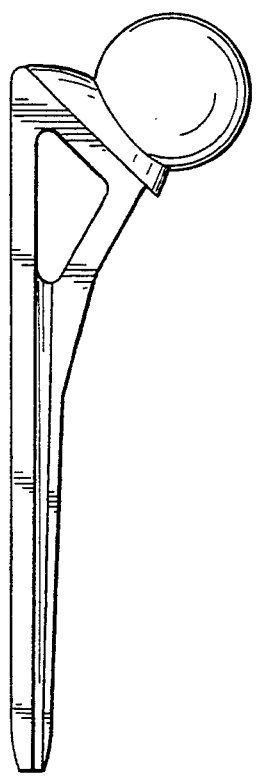
FIG. 1C is a further example of a typical hip joint endoprosthesis.

According to the invention, a zirconium or zirconium alloy unipolar medical implant, such as for example the hip joint implant of FIGS. 1A–C, wherein a femoral head cooperates with and slides against natural cartilage, may have its bearing surface (the femoral head's surface in this case) coated with a layer of blue-black or black zirconium oxide or zirconium nitride to produce a smooth, low friction surface that does not release metal ions into synovial fluid in the joint or surrounding tissue. FIG. 1A depicts schematically a modular hip joint 10, implanted after hemiarthroplasty, into the femur 12 of a recipient. The hip joint 10 has a neck 14 around the proximal end of which is optionally provided a sleeve 16, to facilitate rotatable coupling of the hip joint 10 relative to a modular unipolar femoral head 20. The neck 14 fits snugly into sleeve 16 which in turn fits into a socket 22 in femoral head 20. The femoral head 20 cooperates with acetabular cartilage layers 18 in an acetabular socket 24 in the pelvic hip structure 26 and is able to move slidingly across the cartilage surface as the femoral head 20 rotates in the acetabular socket 24.

While the above description relates to unipolar hip implants, the invention more broadly encompasses all types of endoprostheses (i.e. implants wherein a prosthetic joint implant cooperates slidingly or by rotation or articulation against an opposing surface of natural body tissue, such as bone or cartilage, in the body).

Figure 2:
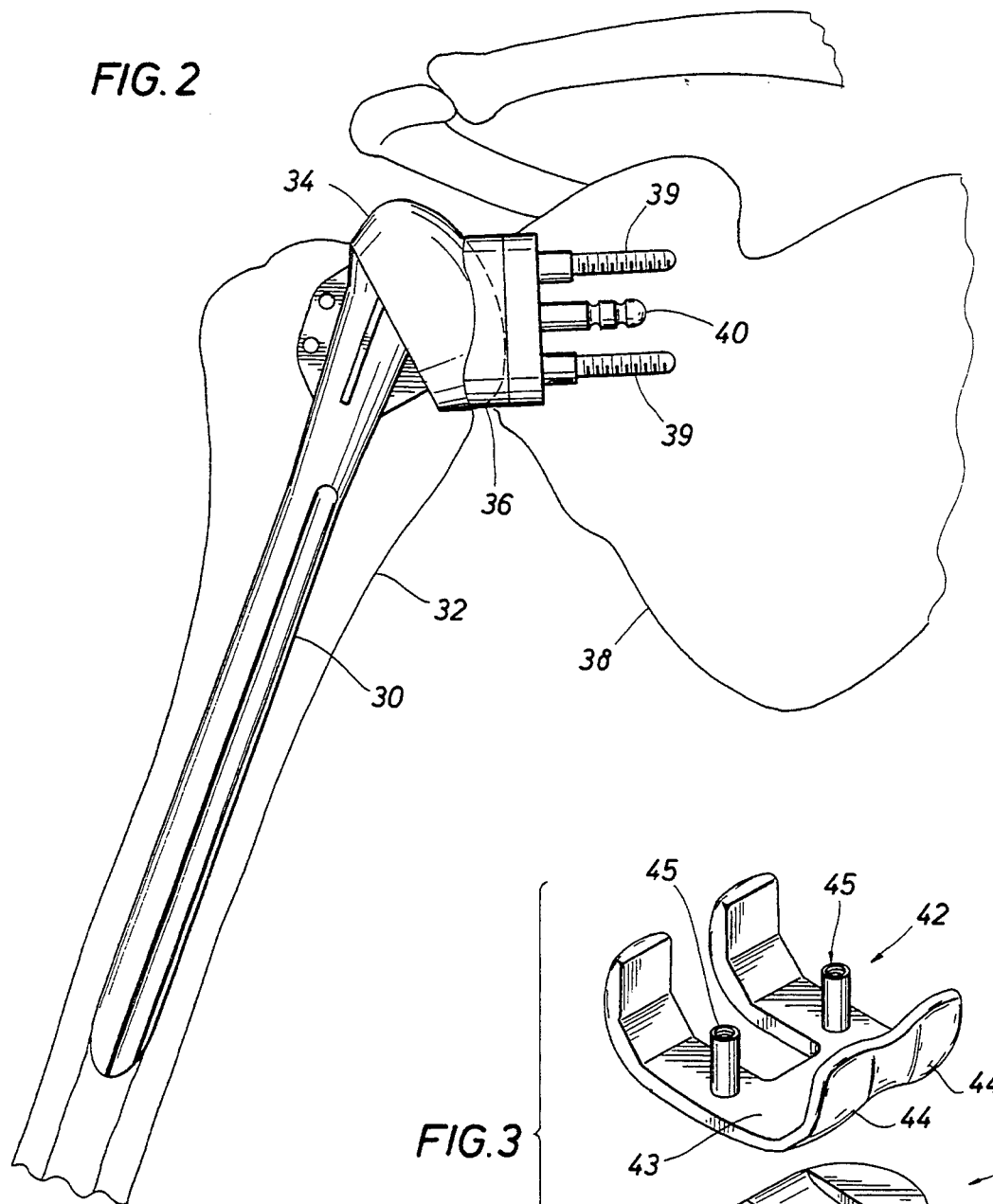
FIG. 2 shows a total shoulder replacement with humeral head cooperating against glenoid component.

Other examples of endoprostheses using the invention coatings include shoulder joints, a total shoulder joint implant is shown in FIG. 2. When an endoprosthetic shoulder joint is utilized, then either the natural glenoid or the natural humerous is retained. In FIG. 2, a humeral component 30 is shown implanted in a humerous 32. The humeral head 34 cooperates with a cavity within a glenoidal implant 36 that is affixed to the scapular 38. Affixation of the glenoidal component 36 to the scapular 38 is achieved by means of pins 39 and a guide-pin 40. When an endoprosthetic humeral component is utilized, the humeral head 34 cooperates against the natural glenoidal tissue. Thus, the invention provides a humeral component wherein at least the portion of the humeral head 34 that cooperates against the natural glenoidal tissue is coated with blue-black or black zirconium oxide or zirconium nitride. On the other hand, if the natural humerous is retained and only the glenoid is removed by hemiarthroplasty, a glenoidal endoprosthesis is implanted. The invention provides a coating of blue-black or black zirconium oxide, or zirconium nitride on at least the surface of the glenoidal cavity that cooperates with the natural tissue of the humeral head. Of course, it is contemplated that the shoulder endoprostheses are fabricated from zirconium or its alloys so that the oxides or nitride may be readily formed on the surface of the prosthesis.

Figure 3:
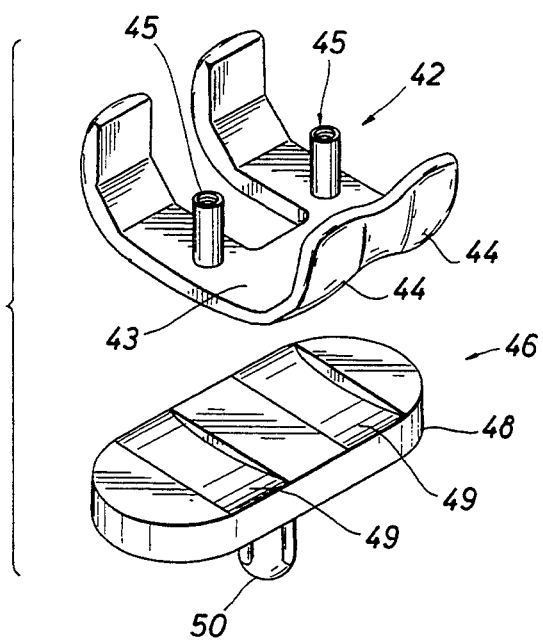
FIG. 3 shows a total knee joint implant with both femoral and tibial components.

As a yet further example of the invention coated prosthesis, FIG. 3 shows two components of a total knee joint replacement. In the event that only the femoral portion of the natural knee must be replaced, then the endoprosthesis would consist of the femoral component 42. Femoral component 42 includes a base 43 supplied with two condylar portions 44 for cooperating with the natural tissue of the tibia. Further, the femoral component 42 is supplied with pins 45 for insertion into drilled holes in the natural femur for holding the femoral component 42 in place. According to the invention, at least the surfaces of the condyles 44 that cooperate with the natural tissue of the tibia must be coated with black or blue-black zirconium oxide or zirconium nitride. In the event, on the other hand, that only the tibial portion of a knee joint is replaced, then a tibial component, show as 46 in FIG. 3, may be implanted as an endoprosthesis. The tibial component 46 includes a base 48 containing two slots 49 designed to cooperate with the natural tissue of the condylar portions of a femur. Further, the base 48 is equipped with at least one pin 50 for insertion into the tibia for affixing the tibial endoprosthesis 46 in place in the body. According to the invention, at least the upper surface, including the surfaces of slots 49, is coated with blue-black or black zirconium oxide or zirconium nitride since these surfaces cooperate with the natural tissue of the condyles.

The invention coatings, when applied to implants that cooperate with natural tissue such as cartilage or bone provides several advantages including reduced friction and wear of the natural tissue than obtained when metallic or bulk ceramic implants are used, and the elimination of metal ion release into surrounding tissue that is found when metallic implants are used. The surfaces of metallic implants tend to corrode as a result of constant, repeated removal and reformation of the passive oxide surface film, over time so that contact or bearing surfaces may gradually become micropitted and roughened. This roughened surface scrapes against the natural tissue, against which it is designed to slide, thereby causing increased tissue damage or, at best, continuous tissue inflammation. Passive layers on the metallic bearing surface are removed gradually, both by mechanical and chemical action in the body during articulation, so that metal below is exposed and releases metal ions into surrounding tissue with potentially adverse medical effects. The invention coated endoprostheses avoid these adverse effects by providing a hard, low friction surface that does not increase in surface roughness with time, or release metal ions by normal sliding action against body tissue as occurs in the case of conventional thin passivation coatings on metallic implants that wear off.

The invention coated endoprostheses also offer significant advantages over conventional implants of this type of bulk ceramic materials. The invention coated metallic implants have a much lower modulus than bulk ceramic (and even certain current metal implants) implants and therefore have superior shock absorbance to protect the natural tissue against which it cooperates and slides. The lower modulus also results in reduced stress shielding and reduced tendency for bone resorption as in the case of surface replacements. Further, the metal-based coated invention endoprostheses have superior impact resistance as compared to bulk ceramics and certain currently used implant metals.

In order to form continuous and useful zirconium oxide or nitride coatings over the desired surface of the metal alloy prosthesis substrate, the metal alloy should contain from about 80 to about 100 wt. % zirconium, preferably from about 95 to about 100 wt. %. Oxygen, niobium, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium containing alloys may be custom formulated by conventional methods known in the art of metallurgy, a number of suitable alloys are commercially available. These commercial alloys include among others ZIRCADYNE 705, ZIRCADYNE 702, and ZIRCALLOY.

The base zirconium containing metal alloys are cast or machined from wrought or forged metal stock by conventional methods to the shape and size desired to obtain a prosthesis substrate. The substrate is then subjected to process conditions which cause the natural (in situ) formation of a tightly adhered, diffusion-bonded coating of zirconium oxide on its surface. The process conditions include, for instance elevated temperature oxidation in air, steam, or water or oxidation in a salt bath or fluidized bed. These processes ideally provide a thin, hard, dense, blue-black or black, low-friction wear-resistant zirconium oxide film or coating of thicknesses typically less than several microns ($10^{-6}$ meters) on the surface of the prosthesis substrate. Below this coating, diffused oxygen from the oxidation process increases the hardness and strength of the underlying substrate metal.

Unlike the prior art titanium oxides of, for example, Steinemann's U.S. Pat. No. 3,643,658, the $ZrO_2$ surface layer is hard, dense, and well attached, and the oxygen supplied to form the blue-black or black zirconium oxide coatings of the invention is a beneficial alloying component which improves the fatigue strength of the underlying zirconium metal thereby increasing the potential life of the prosthesis. In contrast, oxygen in titanium alloys tends to stabilize the lower strength $\alpha$-phase which significantly reduces the metal's fatigue strength.

The air, steam and water oxidation processes are described in now-expired U.S. Pat. No. 2,987,352 to Watson, the teachings of which are incorporated by reference as though fully set forth. The air oxidation process provides a firmly adherent black or blue-black layer of microcrystalline zirconium oxide primarily of monoclinic crystalline form. If the oxidation process is continued to excess, the coating may whiten and separate from the metal substrate. The oxidation step may be conducted in either air, steam or hot water. For convenience, the metal prosthesis substrate may be placed in a furnace having an oxygen-containing atmosphere (such as air) and typically heated at 700°–1100° F. up to about 6 hours. However, other combinations of temperature and time are possible. When higher temperatures are employed, the oxidation time should be reduced to avoid the formation of the white oxide.

While blue-black or black zirconium oxide and nitride coatings of thickness ranging from about 1 to about 25 microns ($10^{-6}$ m) are useful, thicknesses of from about 1 to about 10 microns are preferred and thicknesses of about 1 to about 5 microns are most preferred because of favorable residual compressive stresses within the coating. Furnace air oxidation at 1000° F. for 3 hours will form an oxide coating on Zircadyne 705 about 3–4 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1–4 microns) have better attachment strength.

The thickness of the blue-black or black zirconium oxide coatings on the invention prostheses provides a further distinction between the invention's preferred coatings and the titanium oxide coatings of U.S. Pat. No. 3,643,658 to Steinemann. Titanium oxide films, whether prepared by high temperature (350° C.) oxidation or high current density anodizing, are thin, powdery and loosely adherent. Consequently, these films can be more easily removed under fretting conditions in vivo exposing metal surface to body fluids with resulting metal ion release into the body tissue. The preferred thicker, microcrystalline, more tightly adherent blue-black or black zirconium oxide or zirconium nitride films, by contrast, do not readily spall or separate from the alloy substrate. The diffusion of oxygen into the zirconium alloy substrate below the $ZrO_2$ surface layer provides a natural interlayer to which the zirconium oxide can adhere readily and tightly. Consequently, these preferred zirconium oxide coatings provide excellent protection against corrosion by body fluids and resistance to spallation.

One of the salt-bath methods that may be used to apply the zirconium oxide coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°–800° C. (1022°–1470° C.). However, the lower oxygen levels in the bath produce thinner coatings than for furnace air oxidation at the same time and temperature. A salt bath treatment at 1290° F. for four hours produces an oxide coating thickness of roughly 7 microns.

Whether air oxidation in a furnace or salt bath oxidation is used, the zirconium oxide coatings are quite similar in hardness. For example, if the surface of a wrought Zircadyne 705 (Zr, 2–3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700–2000 Knoop hardness.

Not only does the zirconium oxide coating serve to protect the prosthesis substrate to which it is applied and increase its mechanical strength properties but, as a result of its low friction surface, it also protects those surfaces against which it is in operable contact and consequently enhances the performance and life of the prosthesis.

Because the zirconium oxide coating is firmly bonded to the zirconium alloy prosthesis substrate, it provides a barrier between the body fluids and the zirconium alloy metal thereby preventing the corrosion of the alloy by the process of ionization and its associated metal ion release. Further, the inert, non-conductive $Z_rO_2$ surface layer eliminates potential galvanic reaction with other metallic implants or components of implants (such as the neck or sleeve in FIG. 1).

Oxygen diffusion into the metal substrate during oxidation also increases the strength of the metal. Consequently, a zirconium oxide coated prosthesis may be expected to have a greater useful service life.

In situ oxidation is the preferred method for producing the invention oxide coatings because it allows oxygen diffusion into the metal substrate thereby allowing the formation of a tightly adherent oxide coating while also strengthening the zirconium metal. Other techniques, such as depositing an oxide coating on the prosthesis substrate may also be used but the coatings produced may not be as effective as those produced by the in situ process. Thus, chemical or physical vapor deposition methods may be used, especially those using an ion-assisted deposition method which improve bonding to the metal substrate.

While the above discussion has dealt mainly with blue-black or black zirconium oxide coatings on prostheses, zirconium nitride coatings are also effective in reducing wear on opposing surfaces and preventing corrosion of the underlying substrate by body fluids. Even though air contains about four times as much nitrogen as oxygen, when zirconium or a zirconium alloy is heated in air as described above, the oxide coating is formed in preference to the nitride coating. This is because the thermodynamic equilibrium favors oxidation over nitridation under these conditions. Thus, to form a nitride coating the equilibrium must be forced into favoring the nitride reaction. This is readily achieved by elimination of oxygen and using a nitrogen or ammonia atmosphere instead of air or oxygen when a gaseous environment (analogous to "air oxidation") is used.

In order to form a zirconium nitride coating of about 5 microns in thickness, the zirconium or zirconium alloy prosthesis should be heated to about 800° C. for about one hour in a nitrogen atmosphere. Thus, apart from the removal of oxygen (or the reduction in oxygen partial pressure), or increasing the temperature, conditions for forming the zirconium nitride coating do not differ significantly from those needed to form the blue-black or black zirconium oxide coating. Any needed adjustment would be readily apparent to one of ordinary skill in the art.

When a salt bath method is used to produce a nitride coating, then the oxygen-donor salts should be replaced with nitrogen-donor salts, such as, for instance cyanide salts. Upon such substitution, a nitride coating may be obtained under similar conditions to those needed for obtaining an oxide coating. Such modifications as are necessary, may be readily determined by those of ordinary skill in the art.

Alternatively, the zirconium nitride may be deposited onto the zirconium or zirconium alloy surface via standard physical or chemical vapor deposition methods, including those using an ion-assisted deposition method. It is preferred that the physical or chemical vapor deposition methods be carried out in an oxygen-free environment. Techniques for producing such an environment are known in the art, for instance the bulk of the oxygen may be removed by evacuation of the chamber and the residual oxygen may be removed with an oxygen getter.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

I claim:

1. An endoprosthesis for implantation in a recipient after hemiarthroplasty, the endoprosthesis having a coated bearing surface for slidingly cooperating against body tissue of a recipient, the endoprosthesis comprising:
   (a) an endoprosthesis body formed of zirconium or zirconium alloy, the endoprosthesis body forming one component of a two-component joint and having a bearing surface at least a portion of which is adapted to cooperate with and slide against body tissue of a second joint component; and
   (b) a thin coating, of thickness from about 1 to about 25 microns, applied directly on at least the portion of the bearing surface adapted to cooperate and slide against the body tissue, the coating selected from the group consisting of blue-black zirconium oxide, black zirconium oxide and zirconium nitride; wherein the coating minimizes metal ion release, friction and wear at interfaces between the coated bearing surface and the body tissue.

2. The endoprosthesis of claim 1 wherein the bearing surface is a femoral head of a hip joint endoprosthesis adapted to cooperate with and slide against cartilaginous tissue of a pelvis.

3. The endoprosthesis of claim 2 wherein the coating covers entire outer surfaces of the femoral head.

4. The endoprosthesis of claim 3 wherein the coating thickness is from about 1 to about 10 microns.

5. The endoprosthesis of claim 1 wherein the bearing surface is a head of a humeral implant adapted to cooperate with natural body tissue of a glenoid of a recipient.

6. The endoprosthesis of claim 5 wherein the coating covers entire outer surfaces of the humeral head.

7. The endoprosthesis of claim 6 wherein the coating thickness is from about 1 to about 10 microns.

8. The endoprosthesis of claim 1 wherein the bearing surface is a bearing surface of a glenoid endoprosthesis adapted to cooperate with natural tissue of a humerus.

9. The endoprosthesis of claim 8 wherein the coating covers the entire outer surface of the glenoid head.

10. The endoprosthesis of claim 9 wherein the coating thickness is from about 1 to about 10 microns.

11. The endoprosthesis of claim 1 wherein the bearing surface is a bearing surface of at least one condyle of a femoral component of a knee joint endoprosthesis adapted to cooperate against natural tissue of a tibia.

12. The endoprosthesis of claim 11 wherein the coating covers entire outer surfaces of the condyle.

13. The endoprosthesis of claim 12 wherein the coating thickness is from about 1 to about 10 microns.

14. The endoprosthesis of claim 1 wherein the bearing surface is a bearing surface of a tibial component of a knee joint endoprosthesis adapted to cooperate with natural tissue of condyles.

15. The endoprosthesis of claim 14 wherein the coating covers entire outer surfaces of the tibial component.

16. The endoprosthesis of claim 15 wherein the coating thickness is from about 1 to about 10 microns.

17. An endoprosthesis for implantation in a recipient after hemiarthroplasty, the endoprosthesis having a coated bearing surface for slidingly cooperating against body tissue of a recipient, comprising:
- (a) an endoprosthesis body formed of zirconium or zirconium alloy, the endoprosthesis body forming one component of a two-component joint and having a bearing surface at least a portion of which is adapted to cooperate with and slide against body tissue of a second joint component; and
- (b) a thin coating, of thickness from about 1 to about 10 microns, applied directly on at least the portion of the bearing surface adapted to cooperate and slide against the body tissue, the coating selected from the group consisting of blue-black zirconium oxide, and black zirconium oxide;

wherein the coating minimizes metal ion release, friction and wear at the interface between the coated bearing surface and the body tissue.

* * * * *